United States Patent [19]

Kenna

[11] Patent Number: 4,621,630

[45] Date of Patent: Nov. 11, 1986

[54] GUIDE FOR FEMORAL NECK OSTEOTOMY

[75] Inventor: Robert V. Kenna, Hackensack, N.J.

[73] Assignee: Pfizer Hospital Products Group, Inc., New York, N.Y.

[21] Appl. No.: 485,541

[22] Filed: Apr. 15, 1983

[51] Int. Cl.[4] .................................................. A61F 5/04
[52] U.S. Cl. .................................................. 128/92 VD
[58] Field of Search ................... 3/1, 1.9, 1.91, 1.911, 3/1.912, 1.913; 128/303 R, 305, 92 C, 92 CA, 92 EB

[56] References Cited

U.S. PATENT DOCUMENTS

| 2,737,835 | 3/1956 | Herz | 128/92 EB |
|---|---|---|---|
| 4,187,559 | 2/1980 | Grell et al. | 3/1.913 |
| 4,357,716 | 11/1982 | Brown | 3/1.913 |

FOREIGN PATENT DOCUMENTS 172316 2/1952 Austria .................. 128/92 EB

Primary Examiner—Richard J. Apley
Assistant Examiner—David J. Isabella
Attorney, Agent, or Firm—Charles J. Knuth; Peter C. Richardson; Harold W. Ordway

[57] ABSTRACT

A guide for femoral neck osteotomy comprises a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongate planar surface disposed at an angle of 45° to the axis of the rod. In use, the rod is aligned with the long shaft axis of the femur and attached to the femur at the greater trochanter. The rod is manipulated until the support arm and the long shaft axis of the tibia are disposed in the same plane. This procedure properly positions the elongate planar surface of the guide bar whereby an instrument in engagement with that surface traverses the femoral neck at an angle of 45° to the long shaft axis of the femur.

13 Claims, 11 Drawing Figures

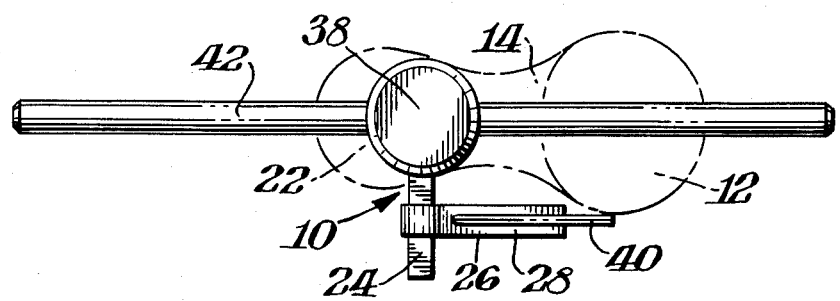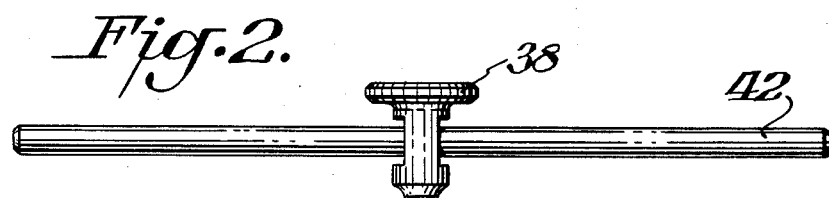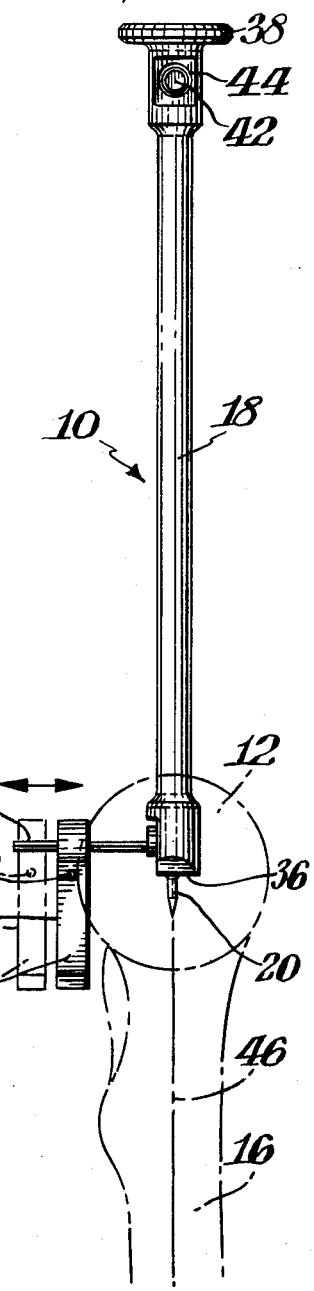

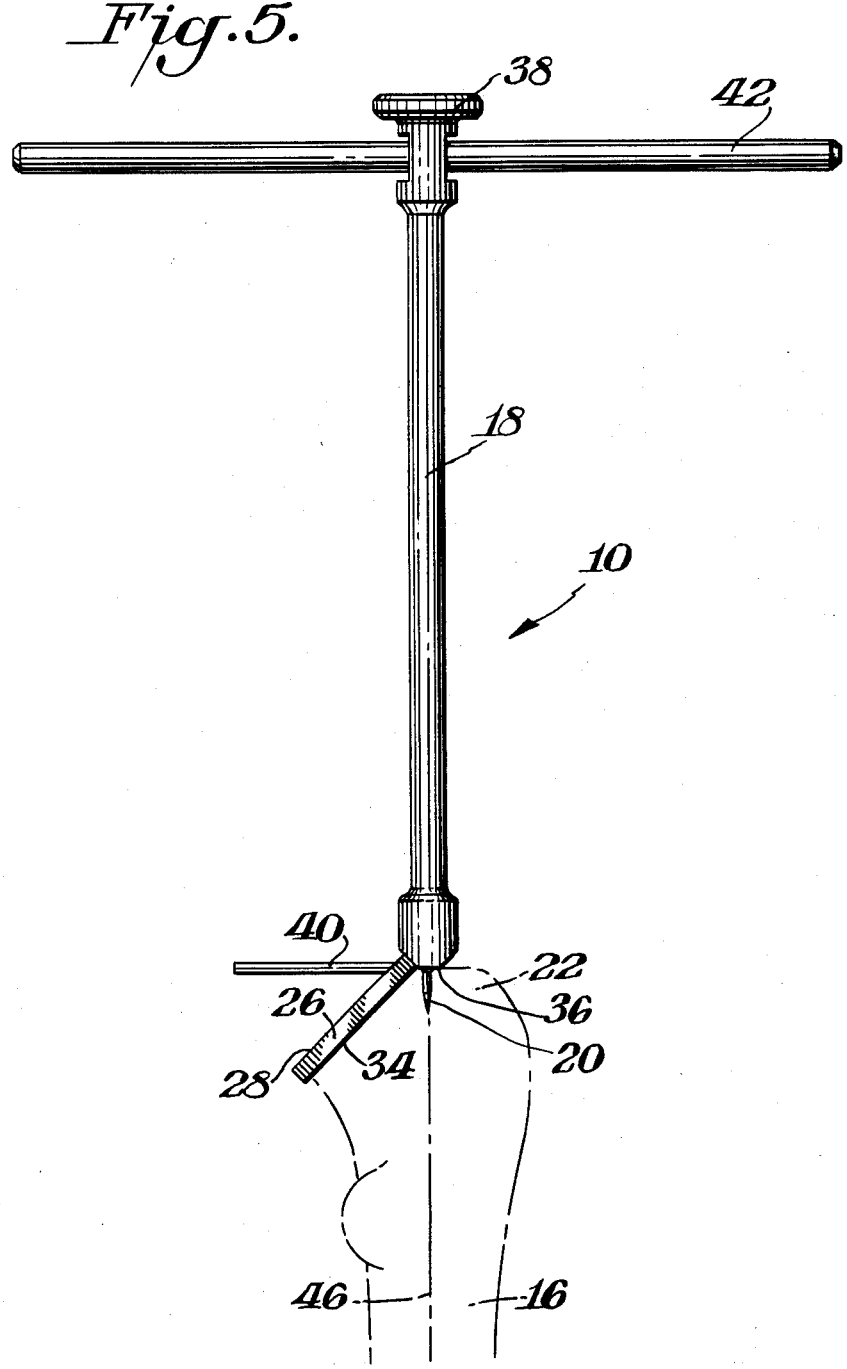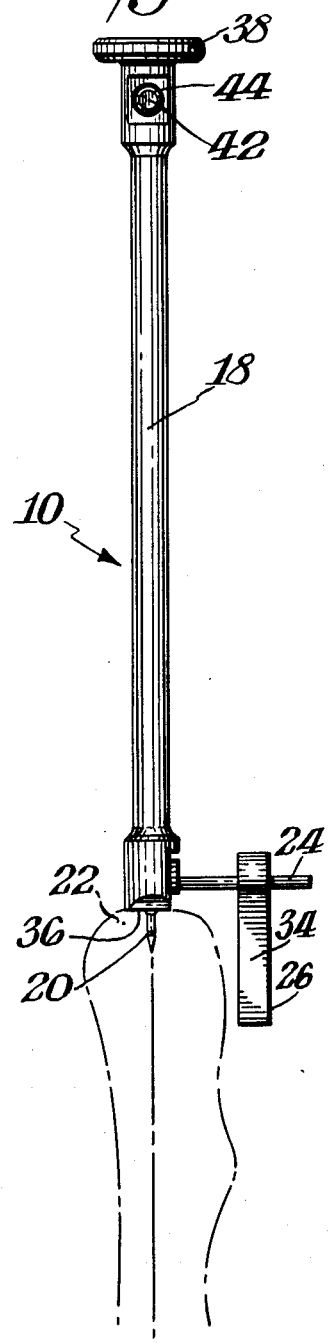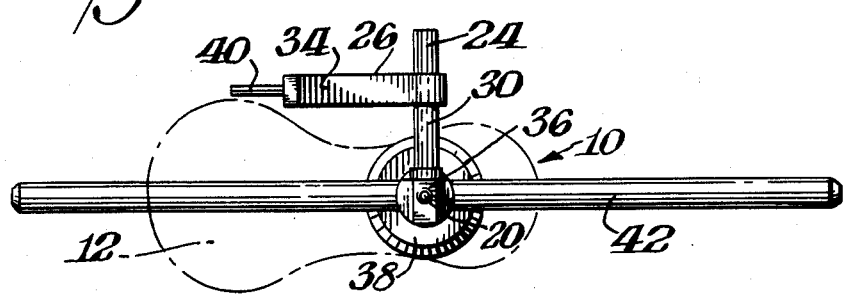

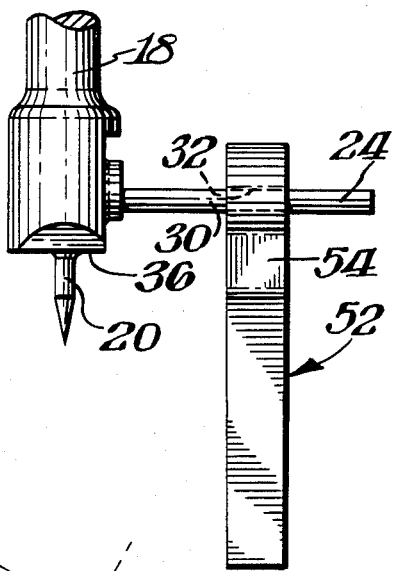
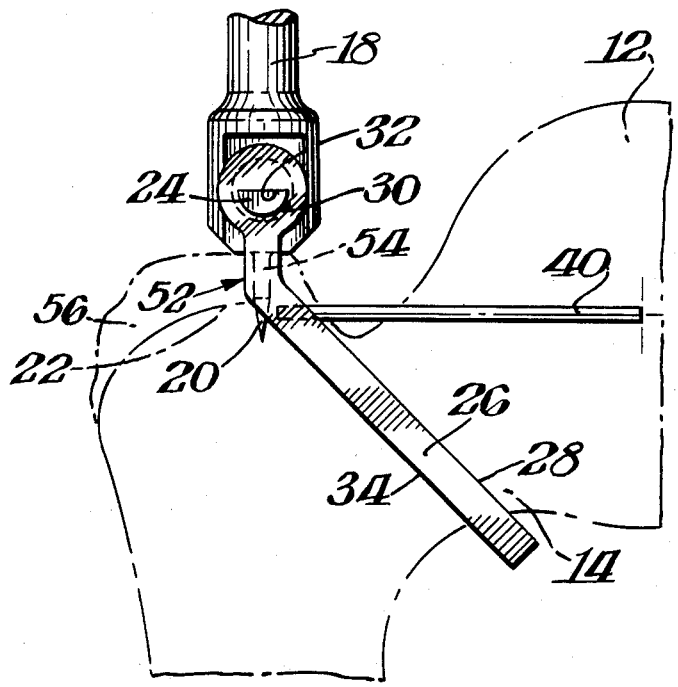
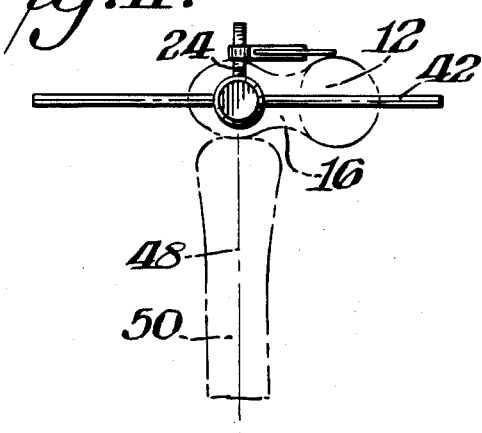

GUIDE FOR FEMORAL NECK OSTEOTOMY

BACKGROUND OF THE INVENTION

The present invention relates to femoral neck osteotomy, and more particularly to a guide and method for cutting a femoral neck at an angle of 45° to the long shaft axis of the femur.

By way of explanation and as used throughout, the femur extends from the hip to the knee. At the upper end, the femur articulates with the acetabulum by a rounded head connected with the shaft of the bone by an oblique neck. A pair of eminences called trochanters are located at the junction of the neck and shaft for the attachment of muscle. The great or greater trochanter is situated at the outer part of the upper end of the shaft at its junction with the neck, and the less or lesser trochanter is at the lower back part of the junction of the shaft and neck. Below, the femur articulates with the tibia by a pair of condyles.

Hip arthroplasty procedure includes anesthesia and patient placement on a table in proper orientation. The patient's body is then stabilized, scrubbed, prepared and draped. An incision is made and the subcutaneous tissue is divided. Appropriate soft tissue is excised and/or divided for exposure and dislocation of the hip. After the femoral head is dislocated from its associated acetabulum, the head is rotated for better exposure. The next step is femoral neck osteotomy wherein the head and neck are cut away from the femur shaft.

The depth of the cut and the cutting plane are most critical and the plane should be 45° to the long shaft axis of the femur. Heretofore, a trial hip prosthesis was used as a guide for estimating the location and direction of the cut. Utilizing this procedure, the femoral trial was simply placed over the proximal femur after dislocation and the prosthesis collar used as a reference for scribing a cut line on the femoral neck. This step was followed by actually cutting along the scribed line to remove the femoral head and neck. Often the cut was not located in the proper 45° plane, thereby causing an improper interface between the prosthesis collar and the cut edge of the bone and poor stress distribution between the prosthesis and the femur.

SUMMARY OF THE INVENTION

According, an object of the present invention is to provide a guide for femoral neck osteotomy which is free of complexity, easy to use, and both accurate and reliable in locating the proper cutting plane.

Another object of the present invention is a procedure for femoral neck osteotomy which is simple to follow and both accurate and reliable in locating the proper cutting plane.

In accordance with the present invention, a guide for femoral neck osteotomy comprises a longitudinal rod having attaching structure at the lower end thereof for securing the rod to a femur at the greater trochanter. A transversely extending support arm is secured to the longitudinal rod adjacent the lower end thereof, and a guide bar is connected to the arm. The guide bar has at least one elongate planar surface downwardly and outwardly extending at an angle of 45° to the axis of the longitudinal rod.

A keyed connection may be provided between the support arm and the guide bar so that the bar is free to slide on the arm toward and away from the longitudinal rod but is prevented from rotating relative to the arm. Such keyed connection may be a semicircular cross section on the support arm and a semicircular bore on the guide bar for mating engagement with the arm.

The guide bar may include two elongate planar surfaces spaced from and parallel to each other. Moreover, the elongate planar surfaces may comprise opposite surfaces on the guide bar. Also, the guide bar may include a downwardly extending interconnecting portion between the elongate planar surface and the point of connection of the bar to the support arm.

The attaching structure at the lower end of the longitudinal rod may comprise a spike, and a strike plate may be located at the upper end of the rod for driving the spike into the femur at the greater trochanter. The lower end of the longitudinal rod may include a transverse flat surface with the spike downwardly extending from that surface and having a longitudinal axis aligned with the longitudinal axis of the rod.

A straight edge may be connected to and outwardly extend from the guide bar for locating the center of the femoral head. The straight edge extends at an angle of 90° to a reference plane defined by the axes of the support arm and the longitudinal rod. Also, when the lower end of the longitudinal rod includes a transverse flat surface, the point of connection of the straight edge to the guide bar is at the same elevation as that surface.

A transversely disposed alignment bar may be connected to the longitudinal rod at the upper end portion thereof. The aligment bar extends at an angle of 90° to the axis of the support arm and is used to assist in properly positioning the cutting guide relative to the femur.

The invention herein also includes a method for cutting the femoral neck at an angle of 45° to the long shaft axis of the femur for removal of the neck and femoral head. Such method comprises the steps of aligning the axis of the longitudinal rod with the long shaft axis of the femur and attaching the rod to the femur at the greater trochanter. The transverse support arm secured to the longitudinal rod at the lower end portion thereof is then positioned so that the axis of the arm and the long shaft axis of the tibia are disposed in the same plane. Such orientation of the longitudinal rod and support arm position the elongate planar surface on the guide bar at an angle of 45° to the long shaft axis of the femur. By guiding a cutting instrument against the femoral neck while the instrument is in engagement with the elongate planar surface of the guide bar, the instrument traverses the neck at a proper angle of 45° to the long shaft axis of the femur.

An additional position check may be made with the transversely disposed alignment bar connected to the upper end portion of the longitudinal rod 90° out of phase with the axis of the support arm. Here the alignment bar is positioned so that a plane passing through the axis thereof and the axis of the longitudinal rod is perpendicular to the plane defined by the long shaft axis of the tibia and the axis of the support arm.

BRIEF DESCRIPTION OF THE DRAWING

Novel features and advantages of the present invention in addition to those mentioned above will become apparent to those skilled in the art from a reading of the following detailed description in conjunction with the accompanying drawing wherein:

FIG. 2 is a front elevational view of the guide with the guide attached to a femur shown in phantom outline;

FIG. 3 is a right side elevational view of the guide;

FIG. 4 is a top plan view of the guide;

FIG. 5 is a rear elevational view of the guide with the guide attached to a femur but with the femoral head removed;

FIG. 6 is a left side elevational view of the guide;

FIG. 7 is a bottom plan view of the guide;

FIG. 8 is a front elevational view similar to FIG. 2 but illustrating a slightly modified guide;

FIG. 9 is a left side elevational view of the guide shown in FIG. 8;

FIG. 10 is an elevational view of the guide shown in FIGS. 1–7 illustrating the proper position of the guide relative to the long shafts of the femur and tibia; and FIG. 11 is a top plan view of the guide attached to the greater trochanter and viewed in the direction of line 11—11 of FIG. 10.

DETAILED DESCRIPTION OF THE INVENTION

Figure 1:
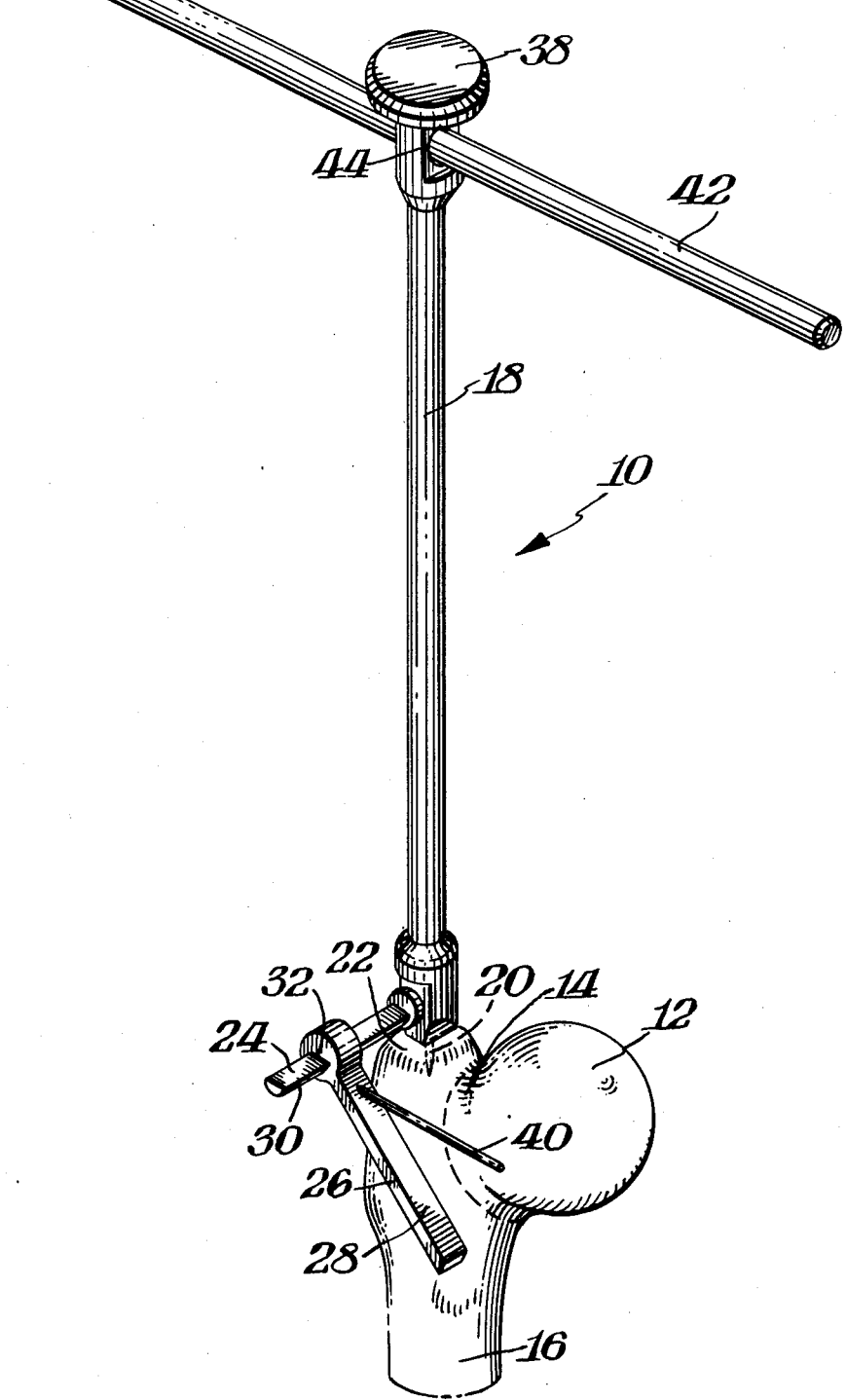
FIG. 1 is a pictorial view of a guide for femoral neck osteotomy, according to the present invention, illustrating the guide attached to a femur at the greater trochanter.

Referring in more particularity to the drawing, FIG. 1 illustrates a guide 10 for performing a femoral neck osteotomy where the femoral head 12 and neck 14 are cut away from the shaft of a femur 16. The guide 10 comprises a handle in the form of a longitudinal rod 18 having structure 20 at the lower end thereof for attaching the longitudinal rod 18 to the femur 16 at the greater trochanter 22. A transversely extending support arm 24 is secured to the longitudinal rod 18 adjacent the lower end thereof, and a guide bar 26 is connected to the support arm 24. The guide bar 26 has an elongate planar surface 28 which, as shown in FIG. 2, extends downwardly and outwardly at an angle A of 45° to the axis of the longitudinal rod 18.

As shown best in FIGS. 1 and 2, the support arm 24 has a semicircular cross section 30 and the guide bar 26 includes a semicircular bore 32 constructed and arranged for mating engagement with the semicircular cross section 30 of the support arm 24. The interrelationship between the semicircular cross section 30 and the semicircular bore 32 provides a keyed connection between the support arm 24 and guide bar 26 so that the guide bar 26 is free to slide on the support arm 24 toward and away from the longitudinal rod 18 but is prevented from rotating relative to the support arm 24.

For reasons which will become apparent from the description below explaining use of the guide 10, the guide bar 26 includes a second elongate planar surface 34 spaced from and parallel to the elongate planar surface 28. In the preferred form of the invention illustrated in the drawing, the elongate planar surfaces 28,34 comprise opposite parallel surfaces on the guide bar 26.

The attaching structure 20 at the lower end of longitudinal rod 18 may be in the form of a spike downwardly extending from a transverse flat surface 36 with the longitudinal axis of the spike aligned with the axis of the longitudinal rod 18. A strike plate 38 is located at the upper end of the longitudinal rod 18 to assist in driving the spike 20 into the greater trochanter 22 of the femur 16.

Guide 10 also includes a straight edge in the form of a pin 40 connected to and outwardly extending from the guide bar 26 for locating the anatomical center of the femoral head 12. As shown best in FIGS. 2 and 4, the pin 40 extends at an angle of 90° to a reference plane defined by the axes of the support arm 26 and longitudinal rod 18. For reasons explained below, the transverse flat surface 36 at the lower end of the longitudinal rod 18 and the point of connection of the pin 40 to guide bar 26 are located at the same elevation.

A transversely disposed alignment bar 42 is connected to the longitudinal rod 18 at the upper end thereof. As shown best in FIGS. 2–4, the alignment bar 42 extends through a boring 44 in the longitudinal rod 18 at an angle of 90° to the axis or transverse direction of the support arm 24. The alignment bar 42 is used to assist in properly positioning guide 10 relative to the femur 16.

Guide 10 is used for cutting the femoral neck 14 at an angle of 45° to the long shaft axis 46 of the femur 16 for removal of the femoral neck 14 and femoral head 12. A 45° cutting plane is important because it provides a proper interface between the prosthesis and the cut edge of the bone, thereby providing excellent stress distribution between the prosthesis and the femur 16. In hip arthroplasty procedure, after the femoral head 12 is dislocated from its associated acetabulum, the femoral head 12 is rotated for better exposure, and the next step is femoral neck osteotomy where the femoral head 12 and neck 14 are cut away from the shaft of the femur 16.

Longitudinal rod 18 is attached to the femur 16 by driving the spike 20 into the greater trochanter 22. This is accomplished by striking the plate 38 at the upper end of the longitudinal rod 18. Before the longitudinal rod 18 is so attached, the guide 10 is properly aligned so that the elongate planar surface 28 extends at a correct angle of 45° to the long shaft axis 46 of the femur 16. Referring to FIGS. 10 and 11, such positioning of the guide 10 is accomplished by aligning the axis of the longitudinal rod 18 with the long shaft axis 46 of the femur 16. The longitudinal rod 18 is simply sighted in the median-lateral and anterior-posterior planes until the longitudinal axis thereof is aligned with the long shaft axis 46 of the femur 16, the overall length of the longitudinal rod 18 facilitating the sighting procedure. Additionally, the longitudinal rod 18 is manipulated to a position where the axis of support arm 24 and the long shaft axis 48 of the tibia 50 are disposed in the same plane. This is accomplished by sighting the support arm 24 and tibia axis 48 in the direction of FIG. 11 until they are aligned. As a result, the axis of the longitudinal rod 18, the long shaft axis 46 of the femur 16, the axis of support arm 24 and the long shaft axis 48 of the tibia 50 are all located in the same plane. Such positioning of the guide 10 relative to the femur 16 and tibia 50 properly positions the elongate planar surface 28 at a 45° angle to the long shaft axis 46 of the femur 16. After sliding the guide bar 26 along the support arm 24 to a position close to the femoral neck 14, an instrument (not shown) is guided against the neck while the instrument is in engagement with the elongate planar surface 28 of the guide bar 26. The instrument traverses the femoral neck 14 at an angle of 45° to the long shaft axis 46 of the femur 16. Such instrument may be a saw blade, bovie, marking pencil, or the like.

Alignment bar 42 is also used to assist in properly locating guide 10 relative to the femur 16. In this regard, the guide 10 is correctly positioned when a plane passing through the axis of the alignment bar 42 and the axis of longitudinal rod 18 is perpendicular to a plane defined by the long shaft axis 48 of the tibia 50 and the axis of support arm 24. Referring to FIG. 10, if the long shaft axis 48 of the tibia 50 and the axis of the support arm 24 define a horizontal plane, the plane passing through the axis of the alignment bar 42 and the axis of longitudinal rod 18 is vertical and hence perpendicular to the horizontal plane. Additionally, the alignment bar 42 assists in rotating the guide 10 about the axis of the longitudinal rod 18 to position the support arm 24 so that its axis and the long shaft axis 48 of the tibia 50, are in the same plane.

Anatomically, the top of the greater trochanter 22 is generally at the same elevation as the center of the femoral head 12. Hence, by positioning the pin 40 at the same elevation as the top of the greater trochanter 22, the pin 40 may be used to locate the anatomical center of the femoral head 12 regardless of the condition of the femoral head 12, particularly the exterior portions thereof which are often deteriorated. The length of the pin 40 is measured from the free end thereof to the reference plane defined by the axes of longitudinal rod 18 and support arm 24. For example, in the case of a small hip, the length of pin 40 may be 30 mm, while with a medium or large hip, such length may be 35 mm. Selection of the proper guide bar 26 and associated pin 40 is initially determined by X-ray analysis prior to hip arthroplasty. Once the proper guide bar 26 is selected, the free end of the pin 40 locates the anatomical center of the femoral head 12. A perpendicular line from the free end of the pin 40 to the elongate planar surface 28 is measured to determine the depth of cut, and such information is utilized in selecting the proper size prosthesis. The depth of cut is determined by the distance between the anatomical center of the femoral head 12 and the elongate planar surface 28 used to guide the instrument. In those cases where a deeper cut is required, the lower elongate planar surface 34 on guide bar 26 is used.

A slightly modified guide bar 52 may be used in place of guide bar 26. FIGS. 8 and 9 illustrate the modified guide bar 52 and parts similar to guide bar 26 are identified with similar reference characters. The main difference between the guide bars 26,52 is that the modified version 52 includes a downwardly extending interconnecting portion 54 between the elongate planar surfaces 28,34 and the point of connection of the modified guide bar 52 to the support arm 24. While the elongate planar surfaces 28,34 of the modified guide bar 52 are correctly located at an angle of 45° to the axis of the longitudinal rod 18, these surfaces are positioned slightly lower than the corresponding surfaces on the guide bar 26. Modified guide bar 52 is used in those cases where the greater trochanter 22 includes a buildup of soft tissue 56, thereby causing the guide 10 to sit slightly higher when attached to the femur 16.

Guide 10 may be fabricated from any suitable material, such as stainless steel, for example. Also, as shown in FIGS. 1-9 of the drawing, the guide 10 is assembled for use on a right femur, it being understood that the guide 10 is equally suitable for use on a left femur by simply positioning the guide bar 26 on the support arm 24 so that the planar surfaces 28,34 extend to the left rather than to the right. Such positioning is shown in FIGS. 10 and 11 wherein the guide is used on a left femur.

I claim:

1. A guide for femoral neck osteotomy, comprising a longitudinal rod having attaching means at the lower end thereof for securing the longitudinal rod to a femur at the greater trochanter, a tranversely extending support arm secured to the longitudinal rod adjacent the lower end thereof, a guide bar connected to the support arm having at least one elongate planar surface downwardly and outwardly extending at an angle of 45° to the axis of the longitudinal rod, and a keyed connection between the support arm and the guide bar whereby the guide bar is free to slide laterally on the support arm toward and away from the longitudinal rod but is prevented from rotating relative to the support arm.

2. A guide as in claim 1 wherein the support arm has a semicircular cross section and the guide bar includes a semicircular bore for mating engagement with the support arm.

3. A guide as in claim 1 wherein the guide bar includes two elongate planar surfaces spaced from and parallel to each other.

4. A guide as in claim 3 wherein the elongate planar surfaces comprise opposite surfaces on the guide bar.

5. A guide as in claim 1 wherein the guide bar includes a downwardly extending interconnecting portion between the elongate planar surface and the point of connection of the guide bar to the support arm.

6. A guide as in claim 1 wherein the attaching means comprises a spike.

7. A guide as in claim 1 including a strike plate at the upper end of the longitudinal rod.

8. A guide as in claim 1 including a straight edge connected to and outwardly extending from the guide bar for locating the center of a femoral head, the straight edge means extending at an angle of 90° to a reference plane defined by the axes of the support arm and the longitudinal rod.

9. A guide as in claim 8 wherein the lower end of the longitudinal rod includes a transverse flat surface and the point of connection of the straight edge to the guide bar is at the same elevation as the transverse flat surface.

10. A guide as in claim 1 including a transversely disposed alignment bar connected to the longitudinal rod at the upper end portion thereof and extending at an angle of 90° to the axis of the support arm.

11. A method for removal of the neck and head of a femur, comprising the steps of aligning the longitudinal axis of a rod with the long shaft axis of the femur; attaching the rod to the femur at the greater trochanter; positioning a transverse support arm secured to the rod at the lower end portion thereof so that the axis of the support arm and the long shaft axis of the tibia are disposed in the same plane: providing a guide bar on the support arm having an elongate planar surface downwardly and outwardly extending at an angle of 45° to the longitudinal axis of the rod; and guiding a cutting instrument against the femoral neck while the instrument is in engagement with the elongate planar surface on the guide bar, whereby the instrument traverses the femoral neck at an angle of 45° to the long shaft axis of the femur.

12. A method as in claim 11 including the further step of positioning a transversely disposed alignment bar connected to the upper end portion of the rod 90° out of phase with the axis of the support arm so that a plane passing through the axis of the alignment bar and the longitudinal axis of the rod is perpendicular to the plane defined by the long shaft axis of the tibia and the axis of the support arm.

13. A guide for femoral neck osteotomy, comprising a longitudinal rod having attaching means at the lower end thereof for securing the longitudinal rod to a femur at the greater trochanter, a transversely extending support arm secured to the longitudinal rod adjacent the lower end thereof, and a guide bar connected to the support arm having at least one elongate planar surface downwardly and outwardly extending at an angle of 45° to the axis of the longitudinal rod, the lower end of the longitudinal rod including a transverse flat surface and the attaching means comprising a spike downwardly extending from the transverse flat surface and having a longitudinal axis aligned with the axis of the longitudinal rod.

* * * * *